United States Patent [19]
Normann et al.

[11] Patent Number: 5,215,088
[45] Date of Patent: Jun. 1, 1993

[54] THREE-DIMENSIONAL ELECTRODE DEVICE

[75] Inventors: Richard A. Normann, Salt Lake City, Utah; Patrick K. Campbell, Los Altos, Calif.; Kelly E. Jones, Salt Lake City, Utah

[73] Assignee: The University of Utah, Salt Lake City, Utah

[21] Appl. No.: 432,992

[22] Filed: Nov. 7, 1989

[51] Int. Cl.⁵ ............................................. A61B 5/04
[52] U.S. Cl. ................................... 128/642; 128/784
[58] Field of Search ................................. 128/642, 784

[56] References Cited

FOREIGN PATENT DOCUMENTS 8707825 12/1987 World Int. Prop. O. .......... 128/784

OTHER PUBLICATIONS

White et al, "Microelectrodes For Biorecording . . .", Biomedical Electrode Technology, 1974, pp. 159–168.

Primary Examiner—Lee S. Cohen
Attorney, Agent, or Firm—Trask, Britt & Rossa

[57] ABSTRACT

A three-dimensional electrode device is disclosed. The device is useful as a neuron interface or as a cortical implant. A plurality of spire-shaped electrodes, formed of semiconductor material, are associated with a rigid base. The electrodes are electrically isolated from each other at the base. Multiplexing circuitry allows the electrodes to be addressed individually.

9 Claims, 11 Drawing Sheets

THREE-DIMENSIONAL ELECTRODE DEVICE

This invention was made with government support under Grant Number 5-38640-3300 awarded by the National Science Foundation. The government has certain rights in the invention subject to the provisions of 37 C.F.R. §401 and 45 C.F.R. §8.

BACKGROUND OF THE INVENTION

1. Field

The present invention is directed toward a three-dimensional electrode device and a method of manufacturing such a device. The device may be particularly useful for neuron interface, and more specifically as a cortical implant for vision prosthesis.

2. State of the Art

It is well known that messages are transmitted throughout the nervous system by means of electrical signals. Electrical signals are generated by various parts of the body, such as the sensory organs, and are transmitted to the brain. The brain in turn generates electrical signals to control muscular and other activity. Certain devices have been developed to electrically interface with neural tissue to either receive messages from or deliver messages to the neurons.

For example, various attempts have been made to provide a cortical implant to interface with the region of the cortex corresponding to the sense of sight. Using such implants, blind persons have been made to perceive simple sensations of sight in the form of spots of light, referred to as "phosphenes," in simple geometric patterns. Such interface systems typically include a two-dimensional array of flat electrodes.

These attempts have not been completely satisfactory. Two-dimensional arrays reside on the surface of the cortex. However, the neurons that initiate phosphene perception lie somewhat below the surface. The depth of these neurons is believed to be about 1.5 mm. In surface arrays, relatively high current, in the neighborhood of 3 mA is required to stimulate neurons. Such high currents may pose pathogenic problems. In addition, a phenomenon has been experienced in which when two nearby electrodes are energized, signals from the electrodes interact to produce a phosphene at an anomalous geometric position. Such electrode interactions severely limit the number of electrodes that can be used in surface arrays.

To induce in a blind person the perception of sight, it appears necessary to produce a large number of contiguous phosphenes, similar to the way a cathode ray tube produces a complete image by appropriate illumination of a large number of contiguous "pixels" on a television screen. Because of their construction and limited electrode spacing, previously known implants have not produced the sensation of a sufficient number of contiguous phosphenes to produce an acceptable sense of vision.

Also, some means must be provided to address each of the electrodes individually. One approach has simply been to run a wire to each electrode. With even a small to moderate number of electrodes, such a bundle of wires is cumbersome and disadvantageous, since these wires must lead from the blind person's cerebral cortex to some point external to the blind person's head.

Electrode arrays are also used in applications other than as neuron interfaces. For example, various arrays of photoreceptors or light-emitting diodes are used for image sensing or image producing devices. It is often useful to form such arrays of semiconductor material, particularly silicon, because of a wide variety of characteristics that may be imparted to semiconductors by means of such processes as doping, etching, etc. Such arrays are typically formed of "wafers" of semiconductor material. The electrodes on these wafers are formed by conventional photolithographic techniques. Such wafers may have thicknesses of a millimeter or less, with the electrodes formed on such wafers being in the range of a few microns in thickness.

There remains a need for a three-dimensional semiconductor device that has the capability of providing a large number of electrodes that may be addressed individually for signal transmission and/or reception. Such an array would be particularly advantageous as a neuron interface device, such as a cortical implant for vision prosthesis. Such a three-dimensional array of elongated electrodes may be positioned with the active tips of the electrodes at a depth in the cortex where very localized stimulation of or recording from neurons may more effectively take place. Such an array would preferably be strong and rigid. The array would preferably be formed of a semiconductor material, such as silicon, to make use of the unique electrical properties of semiconductors. The individual electrodes would each be preferably addressable without the need for a large number of lead wires, such as by the provision of a multiplexing system.

SUMMARY OF THE INVENTION

The present invention provides a three-dimensional electrode device. This device may be particularly adapted as a neuron interface device, and more specifically, a cortical implant. A base of rigid material is provided. A plurality of elongated electrodes are mounted to the base to extend away from the base. The electrodes are electrically isolated from each other at the base by means of a second material positioned between the electrodes. Each of the electrodes has a distal end. Signal connection means is linked with the electrodes for providing electrical connection to each of the electrodes individually.

The electrodes may advantageously be spire shaped, or tapered from the base toward the distal ends. The electrodes may also advantageously be formed of a semiconductor material, such as silicon. In one embodiment, the electrodes are electrically isolated from each other by means of semiconductor doped with an impurity. In another embodiment, the electrodes are electrically isolated from each other by glass.

The signal connection means may include an electrical gate associated with each of the electrodes. The electrical gates may be arranged in a two-dimensional array and multiplexed to be addressable individually. The electrodes also preferably include a charge transfer material at the distal ends.

The invention also provides a method of manufacturing an electrode device. A three-dimensional chunk of a first material is provided. A first surface of the chunk is impinged to a preselected depth with a second material to provide isolating regions of the second material and isolated regions of the first material between the isolating regions. The second material is adapted to provide electrical isolation between the isolated regions. A second surface of the chunk is sawed opposite the first surface at a preselected depth in criss-crossing channels to provide pillars of the first material between the channels. The pillars are electrically isolated from each other by means of the isolating material. The pillars are tapered to reduce their cross-sectional size toward their distal ends, and the distal ends are metallized.

In one embodiment, the method includes the additional step of positioning electrical gates upon the first surface of the chunk to provide electrical connection to each of the pillars.

In a preferred embodiment, the method further comprises the step of coating the pillars and the base with an ion impermeable material. The semiconductor device may be advantageously used as a neuron interface device. This neuron interface device may be a cortical implant for vision prosthesis.

The first material may be a semiconductor material. In one embodiment, the second material is a semiconductor material doped to provide pn junctions between the first material and the second material. In another embodiment, the second material is glass.

The invention provides an electrode device that has the capability of providing a large number of electrodes that may each individually be addressed for signal transmission and/or signal reception. This device may be particularly advantageous for a neuron interface, and particularly a cortical implant for a vision prosthesis. Since the device is three dimensional, the active tips of the electrodes may be positioned at a depth in the cortex where interface with neurons may more effectively and directly take place. The array is strong and rigid. In preferred embodiments, the array is multiplexed such that only a small number of lead wires need to be attached.

DETAILED DESCRIPTION OF THE ILLUSTRATED EMBODIMENT

Figure 1:
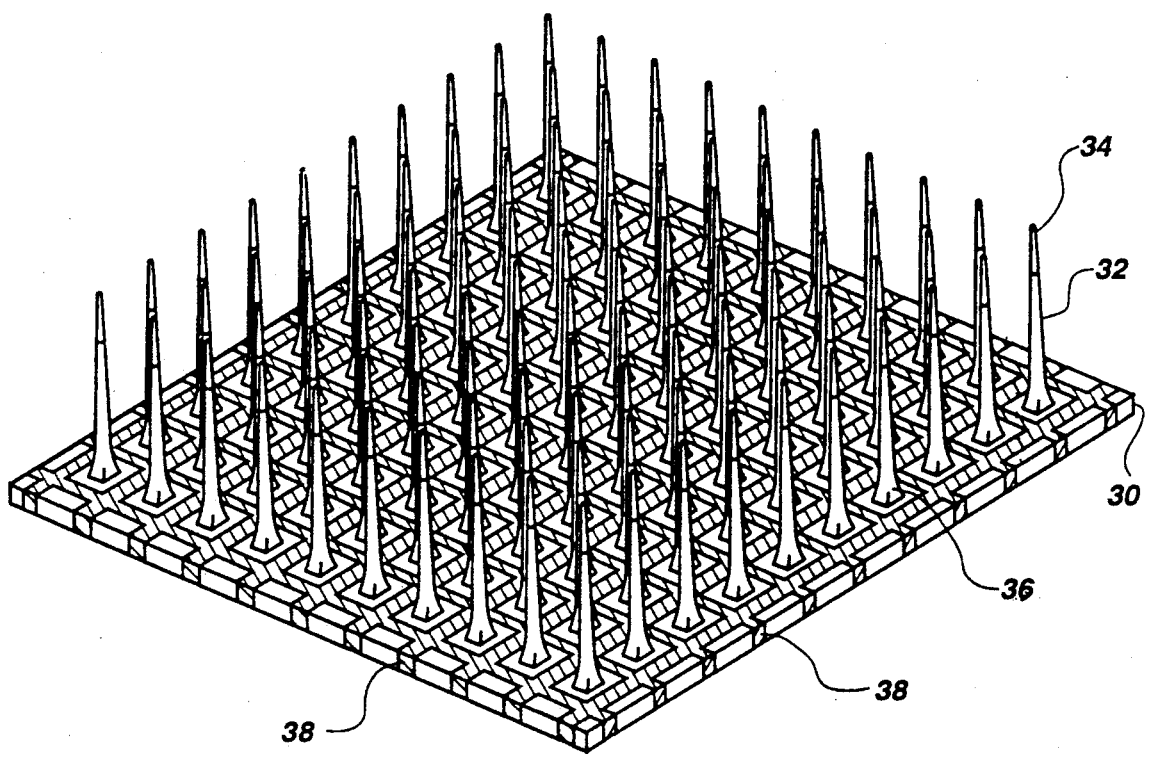
FIG. 1 is a perspective illustration of a semiconductor device of the invention, particularly adapted for neuron interface or vision prosthesis.

FIG. 1 is a perspective illustration of a three-dimensional electrode array of the invention. This electrode array is specifically adapted to be used as a neuron interface device and to be implanted in the cortex of the brain. More specifically, the illustrated electrode array is adapted to be used as a vision prosthesis for a blind person. A visual image is reduced by some means, for example, a video camera, to an electrical signal that is then provided to the electrode array of FIG. 1. This electrical signal is used to control the amplitude of the signal provided to each electrode in the array. An actual image is scanned to produce the series of signals. This series of electrical signals is then multiplexed across the electrode array to produce phosphenes corresponding to the image. The blind person perceives the image in his mind, thus providing a usable sense of sight.

The electrode array of FIG. 1 includes a base 30 to which are connected a plurality of electrodes, of which electrode 32 is typical. As shown, each electrode 32 is spire-shaped. In other words, electrodes 32 are relatively large in cross-sectional size at their bases 36 where they connect to base 30 and taper toward distal ends 34. Electrodes 32 are electrically isolated from each other at base 30. Base 30 and electrodes 32 are formed substantially of semiconductor material, preferably silicon. Electrodes 32 should be at least about 1000 microns in length and preferably are about 1500 microns in length, in order to penetrate outer cortical structures to stimulate the underlying normal inputs to neural structures, which generally lie about 1500 microns below the surface of the cortex.

Figure 2:
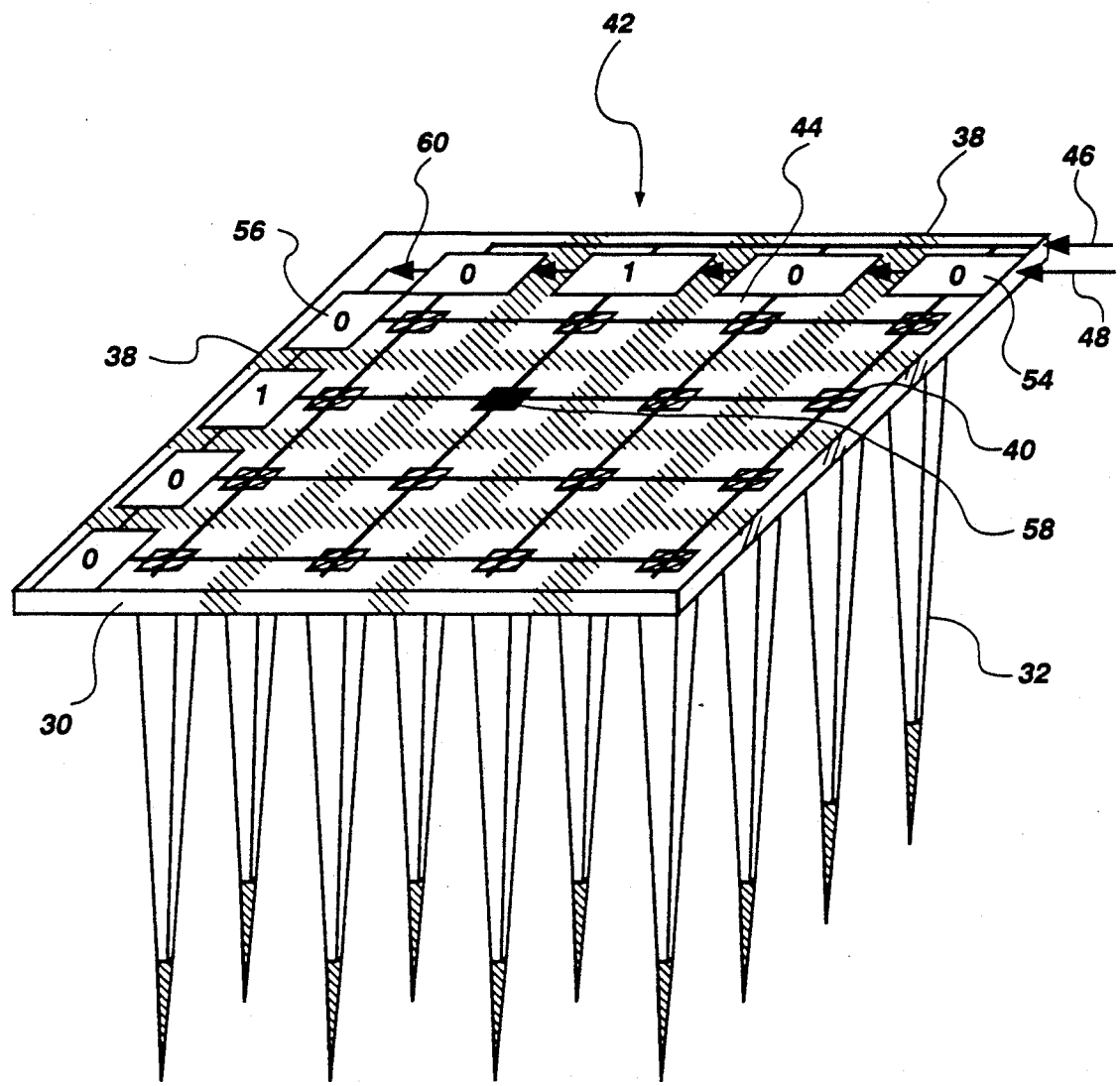
FIG. 2 is a perspective schematic illustration of the device of FIG. 1 showing multiplexing circuitry.

FIG. 2 is a schematic representation of the electrode device of FIG. 1 showing multiplexing circuitry associated with the electrodes 32. A plurality of AND gates, of which gate 40 is typical, are associated with the back side 42 of base 30. Face 42 is a two-dimensional flat plane. Using conventional photolithographic techniques, gates 40 may be formed as two-gate field effect transistors (FET) which are formed over and electrically connected to the projections of each of electrodes 32. Electrodes 32 are electrically isolated one from another by means of channels 38 of isolating material. The portions of base 30 connected to electrodes 32 are isolated regions of which region 44 is typical. As shown, gates 40 are connected to these isolated regions.

The signal produced by the imaging device, such as a video camera, is fed into input 46. The signal is provided to all of the gates 40 at the same time. Whether or not a particular gate is activated to provide this signal to its associated electrode 32 depends on the multiplexing circuitry. Gates 40 allow for bidirectional flow of current through each electrode 32. A clock provides an oscillating series of logic "1" and logic "0" signals at a selected frequency to input 48.

Gates 40 are connected to an X-axis shift register 54 and a Y-axis shift register 56. Shift registers 56 and 58 are linked by a carry 60. The gate 40 that has a "1" logic level on both its respective row and column is energized. In FIG. 2, gate 58 is the energized gate. Gate 58 would therefore provide the electrical signal (which is supplied to all gates 40) to be transmitted only to its associated electrode 32. Thus, shift registers 54 and 56 allow the entire array to be "scanned," one electrode and a time. The implant needs only five wires attached to it: two power supply lines (not shown), a ground (not shown), a clock, and the signal line.

The electrode array is three dimensional. The electrodes are intended to penetrate the cortical tissue and to position the electrode tips 34 near the neurons responsible for phosphene perception. Because the active current-passing tips 34 are in close proximity to these neurons, a relatively lower current can be used for the signal supplied to the array. Such currents can be in the neighborhood of 1 to 100 $\mu$A. The close proximity of tips 34 to the neurons and the lower currents also reduces electrode interaction, thus reducing anomalous phosphene effects and allowing for a higher number of contiguous phosphenes.

The isolation regions 38 are formed in any appropriate manner which provides a rigid and strong base 30. At present, two methods are disclosed for providing such a base having isolation regions. One is thermomigration, and the other is a method that places channels of glass in between the isolated regions 44. The array described includes 100 electrodes. However, a much larger or smaller number of electrodes may be fashioned if it is deemed useful in the particular application involved. The block or "chunk" from which the electrode arrays are fabricated is a 1.7 millimeter thick mono-crystalline n-doped silicon, with a resistivity of 1-10 ohm-cm.

Thermomigration is described generally in U.S. Pat. No. 3,898,106 issued to Cline et al., entitled "High Velocity Thermomigration Method of Making Deep Diodes; High Temperature Melting," the disclosure of which is incorporated herein by reference. The method used in the present invention to achieve thermomigration is similar to that described in U.S. Pat. No. 4,001,047 issued to John K. Boah, entitled "Temperature Gradient Zone Melting Utilizing Infrared Radiation," the disclosure of which is also incorporated herein by this reference.

Figure 3:
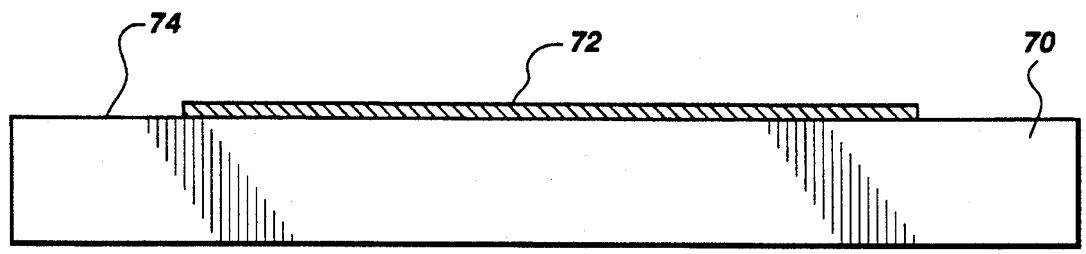
FIG. 3 is a side view of a block with an aluminum layer deposited in preparation for a thermomigration process.
Figure 4:
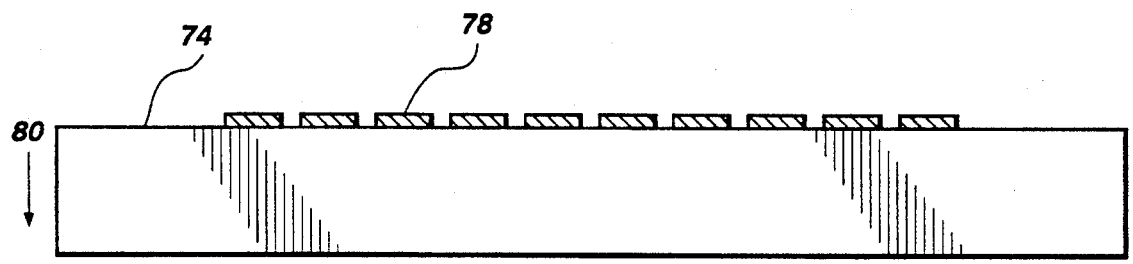
FIG. 4 is a side view of the block of FIG. 3 with aluminum pads having been prepared.
Figure 5:
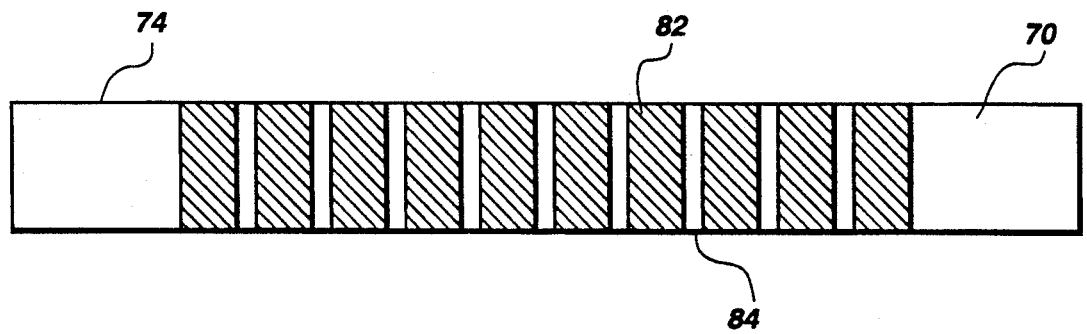
FIG. 5 is a side view of the block of FIG. 4 after the aluminum pads have been thermomigrated through the silicon block.

A description of the thermomigration technique is described in reference to FIGS. 3-5. A block 70 of 1.7 mm thick monocrystalline n-doped silicon is provided having a resistivity of 1-10 ohm-cm. A 6 micron thick layer 72 of aluminum is deposited on back surface 74 of block 70. Back surface 74 will become the surface 42 (FIG. 2) of the array. Referring to FIG. 4, conventional photolithographic/etching techniques are used to form one hundred 300 micron by 300 micron rectangular pads 78. These pads are then annealed to the silicon block 70.

The silicon block 70, now coated with the 100 aluminum pads, is then placed in a thermomigration oven with a positive temperature gradient in the direction of arrow 80. Each pad 78 becomes a localized aluminum-silicon "melt" that propagates in the direction of the temperature gradient through the silicon block 70 in relatively straight columns. The aluminum passing through the silicon leaves behind trace aluminum to form the columns 82 (FIG. 5) of aluminum-doped silicon. After thermomigration is complete, the front surface 84 of the block and the back surface 74 are polished. The aluminum-doped silicon is revealed by a staining procedure. Each p+ doped column 82 forms a diode in block 70 between column 82 and the surrounding n-type block. Therefore, a pair of back-to-back diodes is created between each adjacent pair of columns 82, which become electrodes 32 after the shaping process is complete. Electrical isolation of electrodes 32 is thereby achieved and current leakage between electrodes is limited to back-biased leakage across these diodes.

Figure 6:
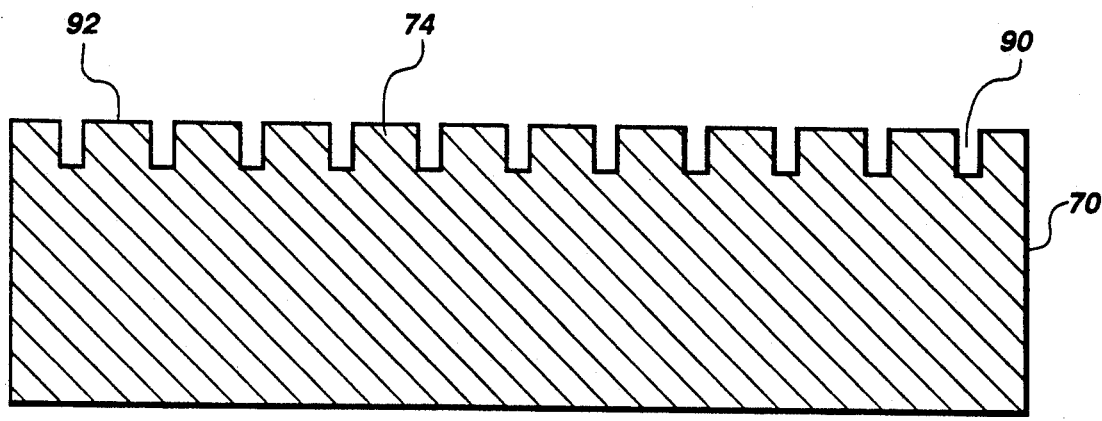
FIG. 6 is a side view of a silicon block with kerfs cut in preparation for a glass melting process.
Figure 7:
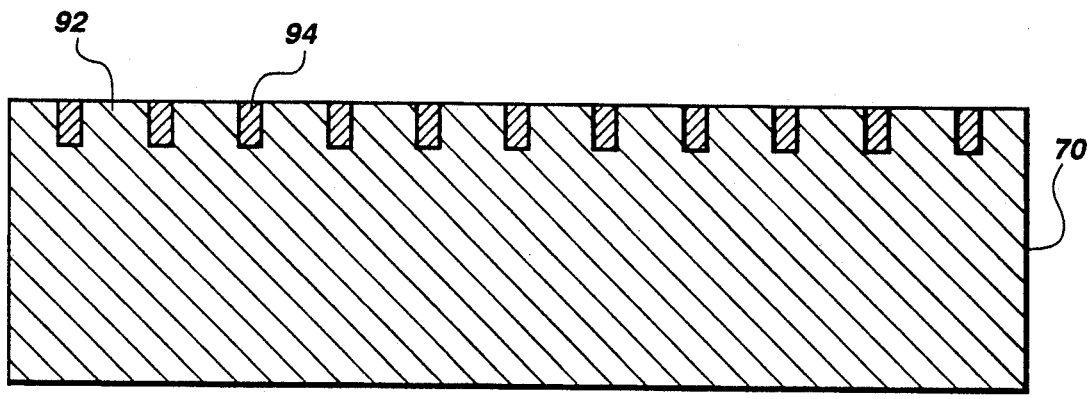
FIG. 7 is a side view of the block of FIG. 6 with glass melted into the prepared kerfs and excess glass removed.

Isolation regions 38 may also be formed by a glass melt process discussed in reference to FIGS. 6 and 7. A diamond dicing saw equipped with a 0.125 mm thick blade, is used to make a series of 0.25 mm deep orthogonal cuts 90 into block 70. Eleven cuts are made with even spacing along one direction. The silicon is rotated 90° and 11 additional cuts are made with the same spacing orthogonal to the first set. This cutting process leaves 100 silicon stubs 92, each 0.25 mm high.

Dicing saws are used in the fabrication of silicon computer chips. Such saws are used to saw apart large numbers of identical chips from a block on which they have formed. In the present application, however, the dicing saw is used to form a three-dimensional structure in the semiconductor block.

Referring to FIG. 7, after stubs 92 are formed, a slurry is prepared of glass frit (Corning Glass Works, 7070), and methyl alcohol. This slurry is dripped onto front surface 74. The alcohol in the slurry wets the silicon surface and carries the glass powder down into the saw kerfs 90. The methanol evaporates quickly. This dripping process is continued until there is a layer of glass powder approximately 0.25 to 0.5 mm above the top surface of stubs 92.

The coated silicon chip or block 70 is then placed in a computer controlled oven. The oven is evacuated and the temperature quickly increased to a temperature sufficient to melt the glass frit, allowing it to flow while not melting the silicon. The temperature is held at this level for 60 minutes, after which the oven is allowed to cool to room temperature. The vacuum in the oven is released and the silicon/glass chip is removed. Any large bubbles in the glass surface are then broken with a sharp probe.

The block 70 is placed in the oven again and the oven is evacuated and the temperature again increased to the same temperature previously used to melt the glass. The temperature is held at this level for 50 minutes, at which time the vacuum is released. Releasing the vacuum forces any bubbles in the glass to shrink in size. The temperature is maintained for an additional 10 minutes, after which the temperature is slowly decreased until the glass is cooled. This melting process removes any large bubbles from the glass and minimizes internal stresses in the glass while assuring good adhesion at the glass/silicon interface. The glass remaining above the level of stubs 92 is then ground off, and the stubs 92 and the glass is then polished to provide a smooth surface as shown in FIG. 7 with regions of glass 94 between stubs 92.

Figure 8:
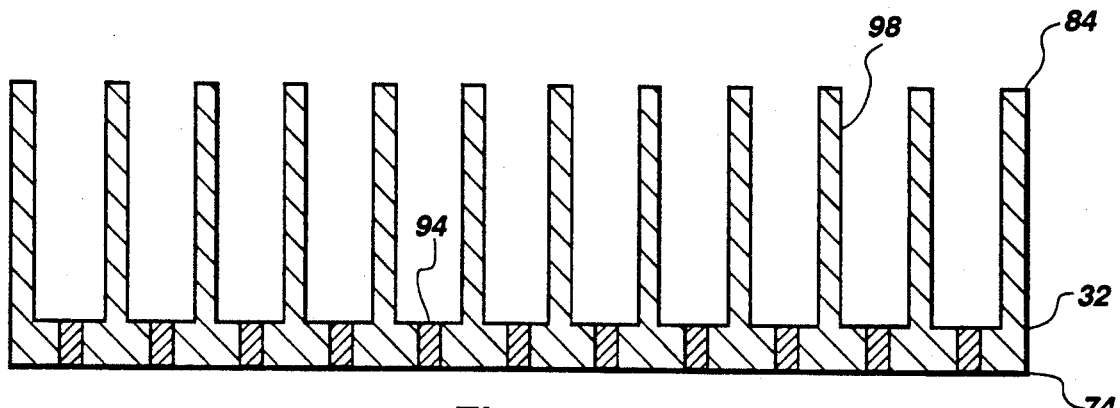
FIG. 8 is a side view of a block after columns have been cut with a dicing saw to prepare electrode columns.

A description of the formation of electrodes 32 is made in reference to FIGS. 8-14. One starts with a block 70 that has had either the thermomigration process performed as discussed in reference to FIGS. 3-5 or the glass isolation region process discussed in reference to FIGS. 6 and 7. The computer-controlled dicing saw is used to produce a series of orthogonal cuts in the silicon block 70. Eleven cuts are made along one axis. The block is then rotated by 90° and 11 more cuts are made orthogonal to the first set of cuts. Each cut is 1.5 mm deep and has a kerf of 270 microns. In thermomigrated blocks, the cutting is aligned between the aluminum-doped columns 82, producing electrodes 32, which are p+ doped. If the glass melt procedure has been used, the cuts are made as shown in FIG. 8 such that the glass regions 94 isolate electrodes from each other.

The dicing process to produce columns 32 is disclosed in terms of orthogonal cuts to produce pillars having square cross-sections. However, pillars having other types of cross-sections may be useful and advantageous. For example, another scheme involves the use of criss-crossing cuts at 60° angular separation to produce a hexagonal array of hexagonally-shaped pillars. Pillars of hexagonal cross-sections may provide electrodes with denser packing than with square pillars.

Figure 9:
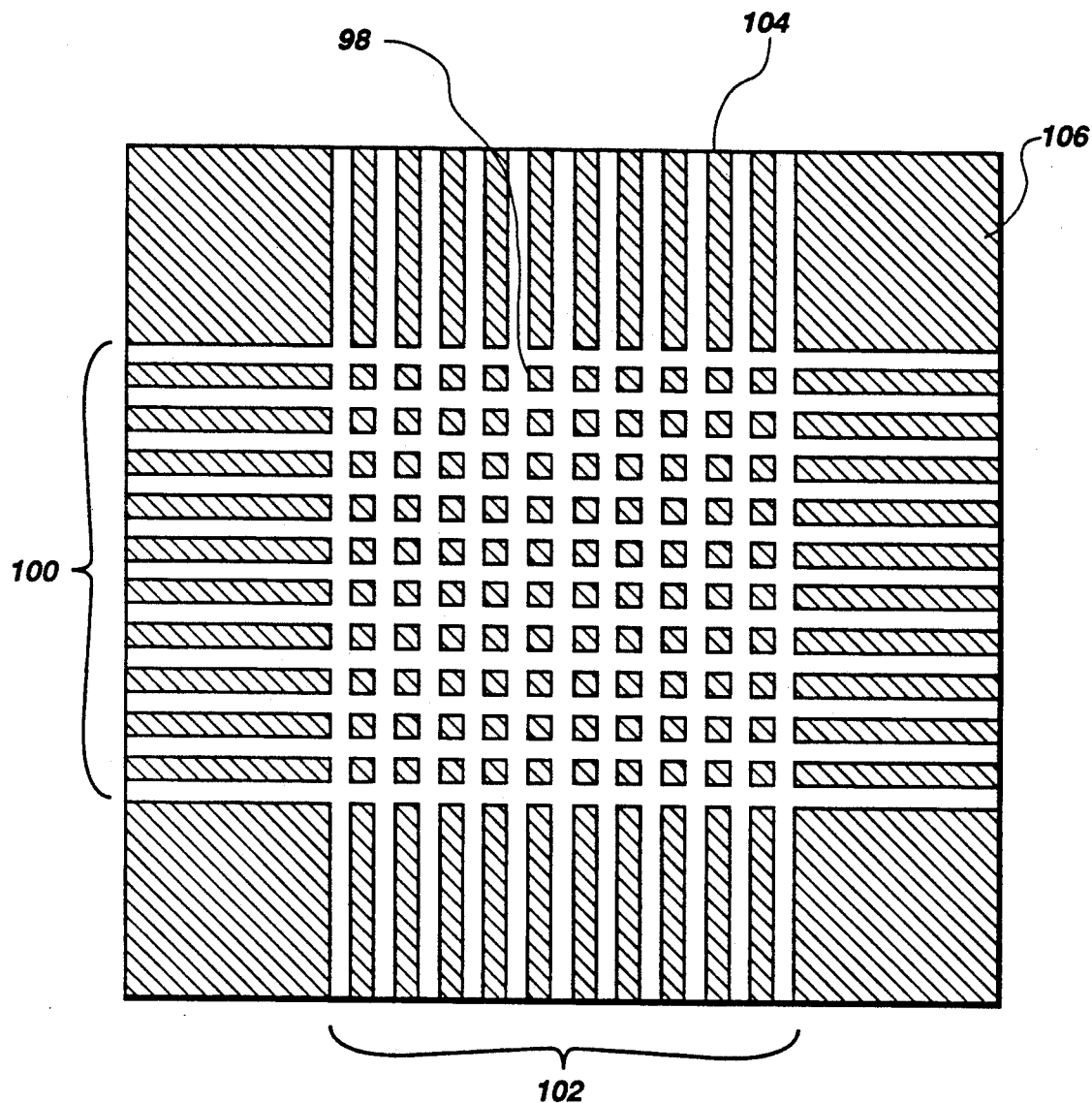
FIG. 9 is a top view of a block after the column dicing process.
Figure 10:
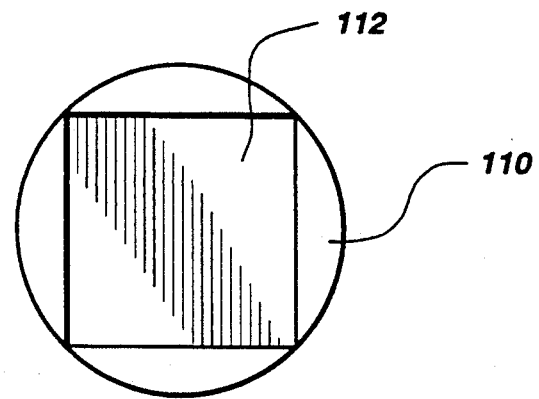
FIG. 10 is a top view of a block holder for the etching process.
Figure 11:
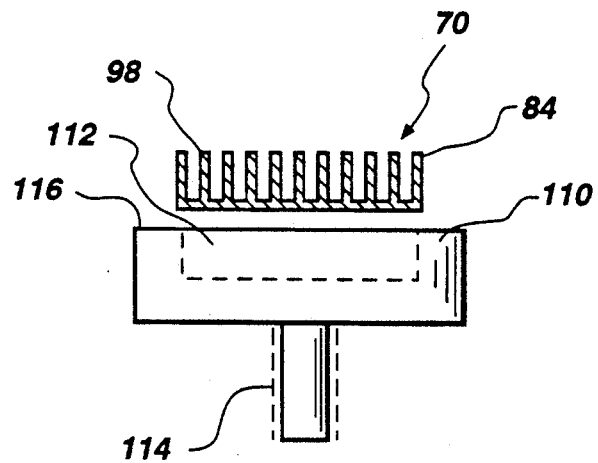
FIG. 11 is a side view of the block holder of FIG. 10.
Figure 17:
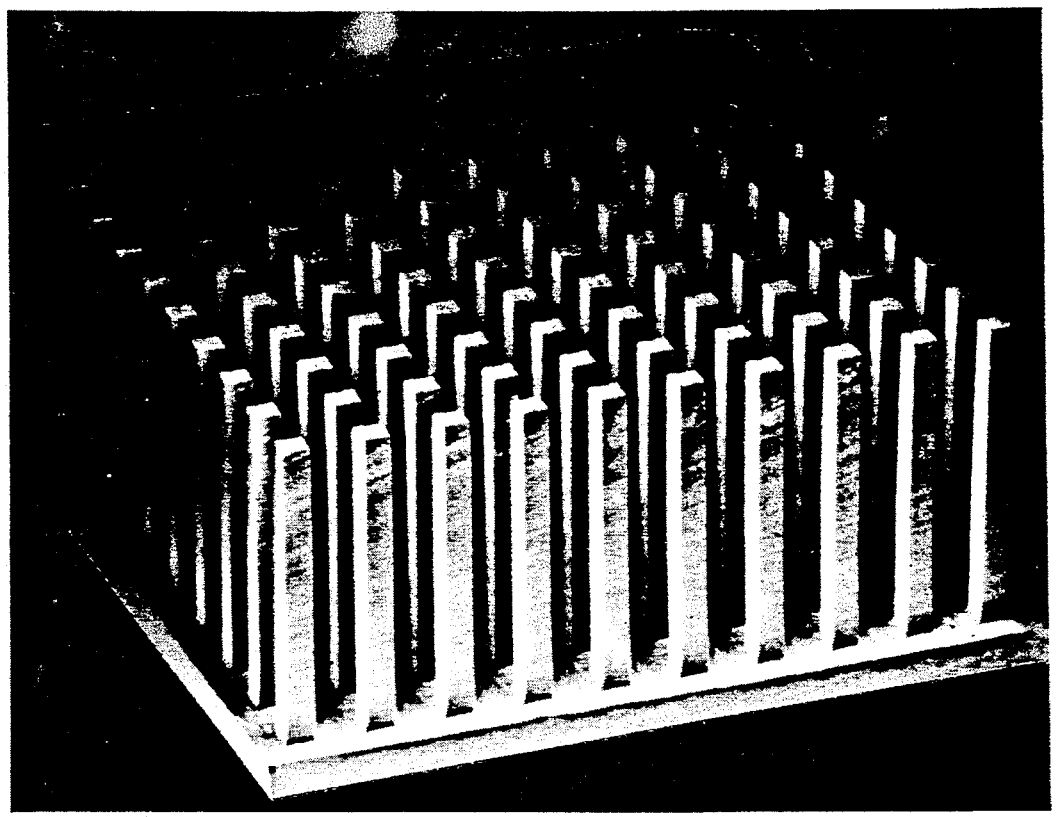
FIG. 17 is a scanning electron micrograph of an array after the dicing process to produce columns.

FIG. 9 illustrates the substrate or block after it has been cut with the dicing saw to produce 100 columns 98 by forming a first set of cuts 100 and a second set of cuts 102 orthogonal to first set 100. As also shown, this cutting process leaves 40 rectangular fins 104 and four corner posts 106. Fins 104 and corner posts 106 are left in place temporarily to facilitate subsequent processing. Cuts 100 and 102 are made from the front side 84 of the block so that the thermomigration or glass melting procedures provides that the electrodes 32 be isolated from each other at base 30. FIG. 17 is a scanning electron micrograph of the array after columns 98 have been formed by the dicing process.

After the columns 98 which form the basis for electrodes 32 have been formed, these columns 98 must be etched to produce pyramid or spire-shaped electrodes 32 as shown in FIG. 1. This etching process is described in reference to FIGS. 10-14. A holder is formed of a cylindrical piece 110 of Teflon that has a diameter of 0.435 inches. A square hole 112 that is 0.25 inches on each side 0.080 inch deep is machined into piece 110. Hole 112 receives block 70 and securely holds it during the etching process. The rectangular block 70 is placed in hole 112 such that block 70 registers in a press- or friction-fit within holder 110. Block 70 is placed such that columns 98 extend toward the opening of hole 112. When block 70 is placed within hole 112, the tops of columns 98 are approximately flush with the upper surface 116 of holder 110.

Figure 13:
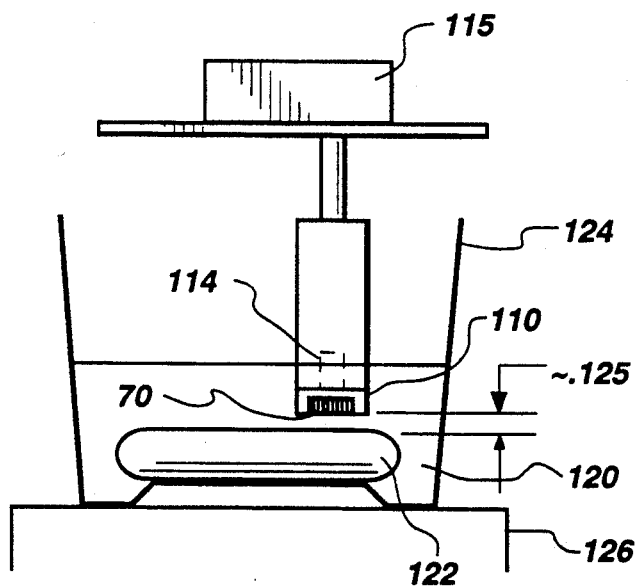
FIG. 13 is a side view of the system of FIG. 12.

Referring to FIG. 13, with block 70 in holder 110, as described, holder 110 is mounted by means of stock 114 to a clock motor 115, and block 70 is immersed in an acid bath of five percent hydrofluoric acid and 95 percent nitric acid etchant 120. Block 70 is positioned approximately 0.125 inches above a magnetic stir bar 122 held within jar 124. Jar 124 has an approximately 1.9 inch diameter. Jar 124 resides on the surface of a magnetic stir plate 126 that has a magnetic mechanism to cause stir bar 122 to rotate at a selected rotational speed.

Figure 12:
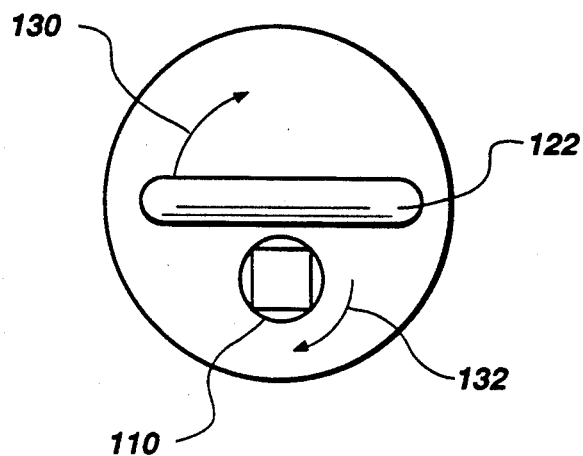
FIG. 12 is a top view of a swirling etch system.
Figure 18:
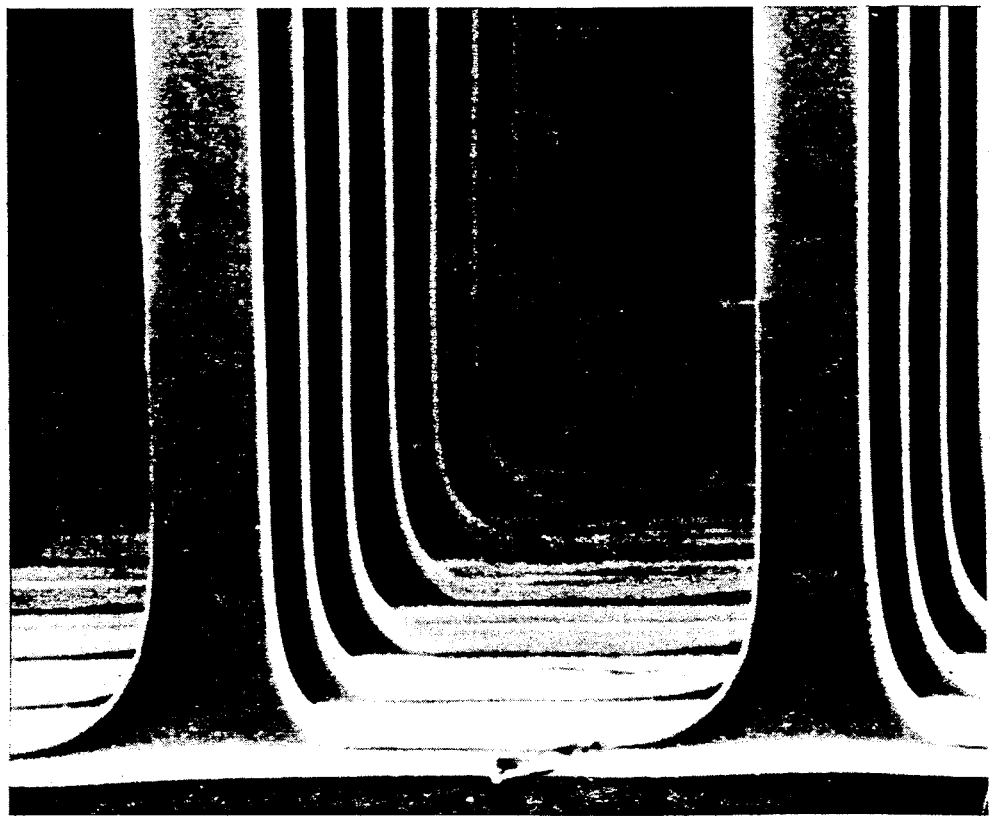
FIG. 18 is a scanning electron micrograph of the base of the columns after the swirl etch process.
Figure 19:
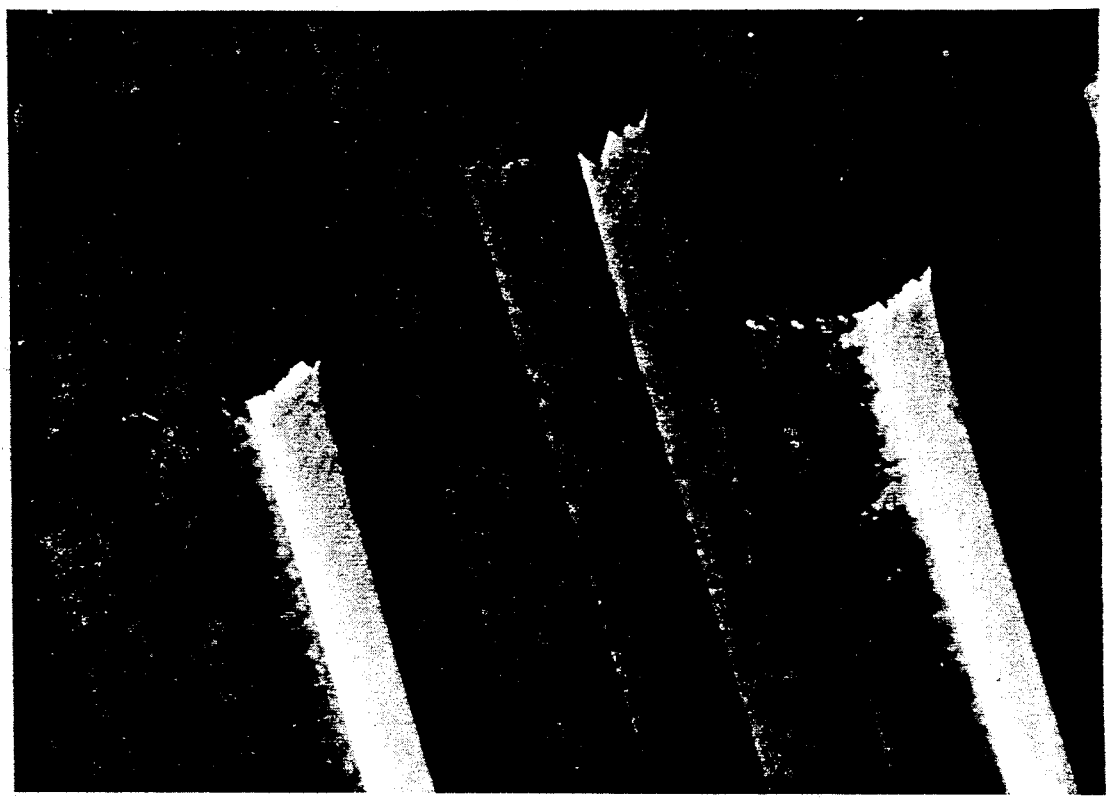
FIG. 19 is a scanning electron micrograph of the tips of the columns after the swirl etch process.

FIG. 12 illustrates a top view of this swirling etch method. Magnetic stir bar 122 is caused to rotate in the direction of arrow 130 at a preferred speed of approximately 375 revolutions per minute. Holder 110 is caused to rotate in the direction of arrow 132 at a rotational speed of approximately 4 revolutions per minute. Block 70 is swirl etched in this manner for approximately three minutes to produce thin columns with polished sides as shown in FIGS. 18 and 19.

Figure 14:
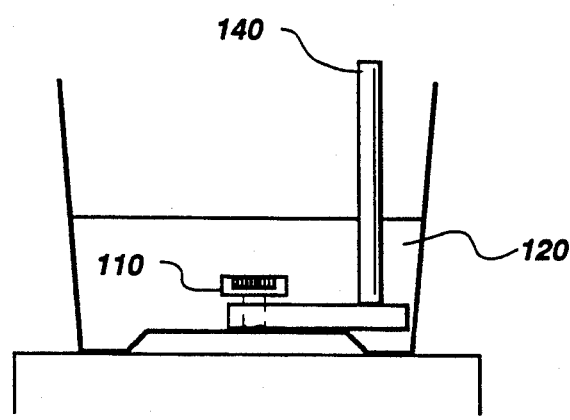
FIG. 14 is a side view of a static etch system.

The final structure of the electrodes is produced by a wet static chemical etching as illustrated in FIG. 14. In this arrangement, holder 110 is placed in an "L"-shaped handle 140 and immersed in the same solution 120 for a period of approximately two to three minutes. The result of this procedure is to sharpen the electrodes to the spire shape shown in FIG. 20.

Figure 20:
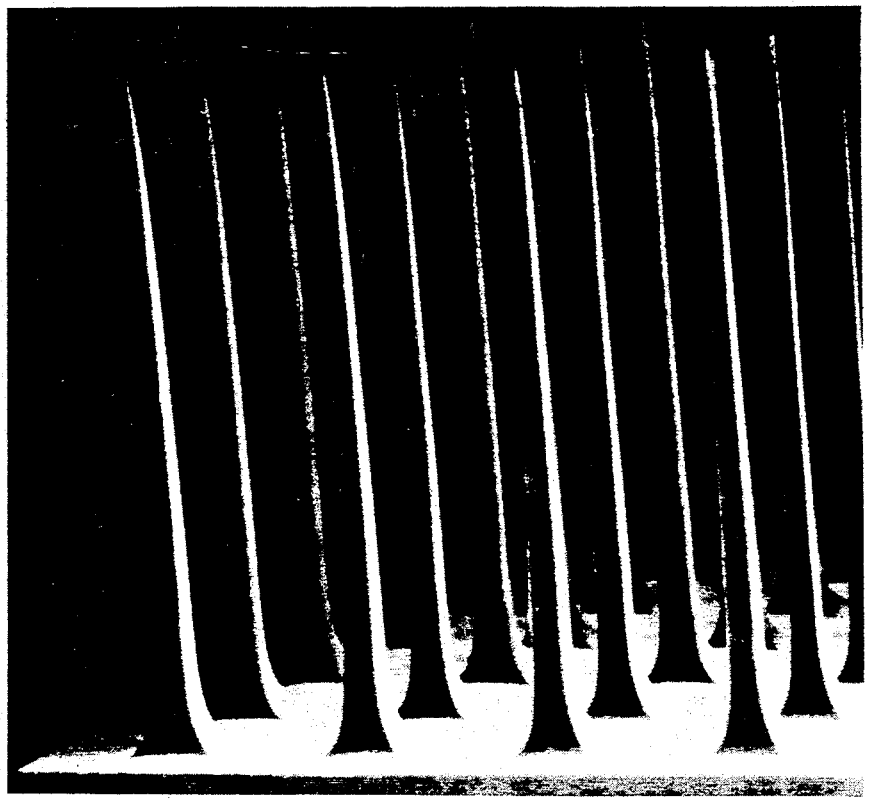
FIG. 20 is a scanning electron micrograph of an array after the static etch process.

As can be seen in FIG. 20, the spires 98 have relatively large cross-sectional sizes at their bases and taper toward their tips. The bases of the columns are roughly square in cross-section because at this point the etchant has had the least effect. These spire-shaped or tapered columns provide for effective insertion of the array into cortical tissue without doing undue harm to the tissue. The columns are pointed at their tips to pierce the tissue and increase gradually in cross-section toward their bases. Thus, after the tips of the electrodes are inserted, the tissue is gradually spread apart until the array is fully inserted. The relatively large cross-sectional size at the base of the electrode provides increased strength for each electrode.

Once the columns 98 have been formed to provide the basis for the electrodes, ohmic contact must be provided to the back of each electrode. A grid of 200 micron by 200 micron square aluminum pads is deposited over the back surface of each column 98. This process is identical to the initial steps of the thermomigration process. These aluminum pads are used whether the thermomigration process or the melted glass process is used to produce the electrodes. The aluminum pads are annealed to the back surface of their respective columns, one pad to each column. This process forms a low resistance ohmic contact to each column 95. At this point fins 104 and corner posts 106 are removed with the dicing saw.

Figure 15:
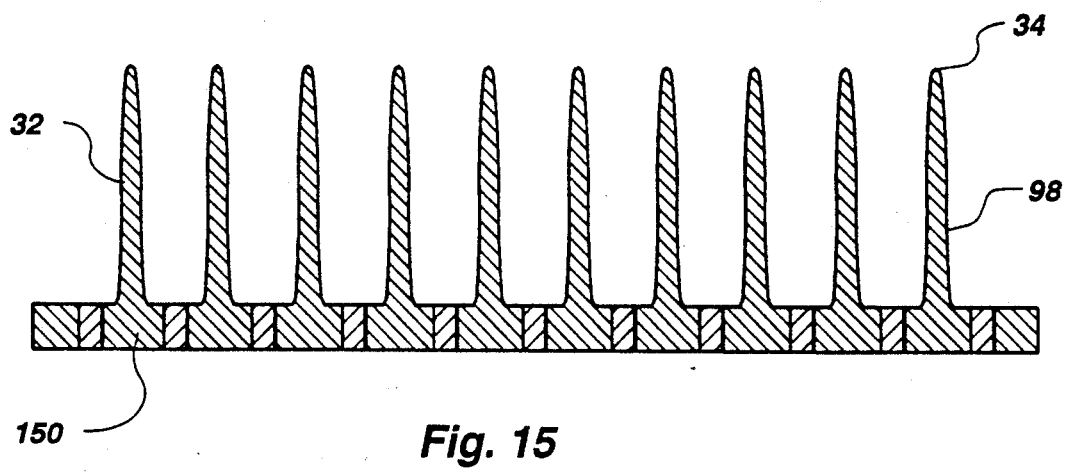
FIG. 15 is a side view of columns etched into electrode shape with the aluminum pads bonded onto the back of each electrode.

Referring to FIG. 15, the tips 34 must be then formed to provide active current passing electrodes. In other words, some means must be provided to transduce electric charge to ionic charge in the neural tissue. In the disclosed array, metal is used as such a charge transfer medium. However, other materials may be used. For example, iridium oxide may be used as an effective charge transfer material. Tips 34 are driven through a metallic foil such that the top 1000 microns of each spire emerge from the surface of the foil. The array, with foil is then transferred to an electron beam evaporator and a few microns of platinum or iridium (which are metallic substances) are deposited on the tips of the electrode. The metal foil is removed, and the array, with its metal coated tips 34 is annealed at low temperature. This annealing drives a small amount of the metal into the silicon and forms a thin layer of metal silicide at the metal/silicon interface. The metal silicide provides an ohmic contact between the metal on the tips 34 and the silicon spires 98. The metal surface forms an active current passing electrode between the silicon and the neurons in the brain.

Figure 16:
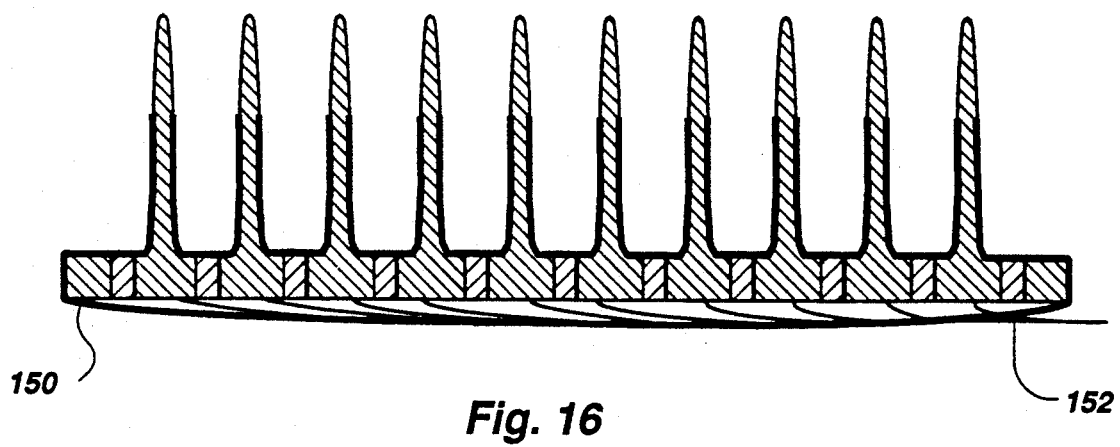
FIG. 16 is a side view of the electrodes of FIG. 15 with lead wires and passivating coating.

Referring to FIG. 16, lead wires 152 are wire bonded to the aluminum pads 150 on the back surface 74 of block 70. This bonding process is a standardized process using ultrasonic bonding of insulated 25 micron gold wires to the aluminum pads 150. The bonded wires are secured to the back side of the array with a layer of polyimide, which is subsequently cured in an oven.

The entire structure (with the exception of the tips 34 of each electrode) must then be insulated or passivated.

Passivation means to coat the array with a substance to prevent ion transfer between neural tissue and the array. In one passivation method, polyimide, coupled to aluminum chelate primer (Hitachi PIQ coupler) is used. The entire array is immersed in aluminum chelate primer and the excess aluminum chelate primer is drained. The entire array with the lead wires is then oven cured.

In an identical fashion, the array is immersed in polyimide and the excess polyimide drained. The entire array with lead wires is then oven cured. The tips of the array are then pushed through a thin foil, and the polyimide and the aluminum chelate primer are etched from the exposed tips of the spires in an oxygen plasma. The 25 micron lead wires is then soldered to a percutaneous connector. The back of the connector is then filled with epoxy.

Another passivation technique involves the use of silicon nitride and silicon dioxide, instead of the polyimide. Silicon nitride, when properly deposited on a silicon dioxide coating, can provide very long-term passivation.

Figure 21:
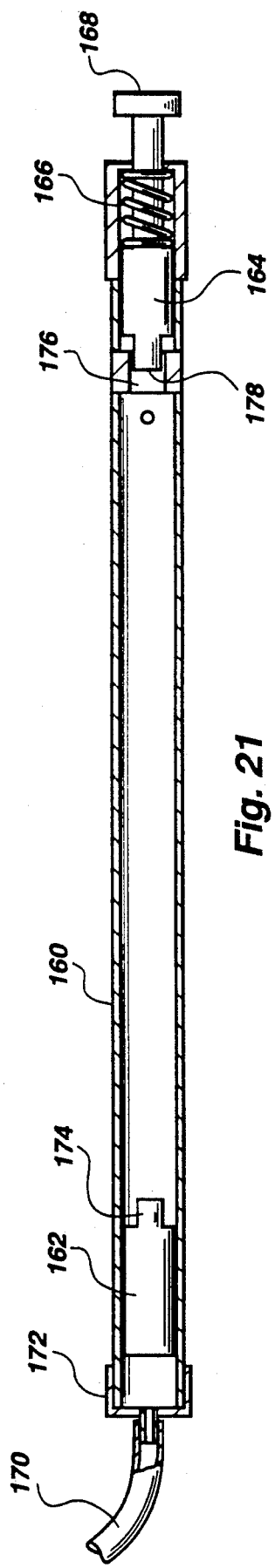
FIG. 21 is a side view of a pneumatic implant inserter of the invention.

FIG. 21 is a side view of a pneumatic impact inserter of the invention. The inserter of FIG. 21 is used to implant the electrode array of FIG. 1 into the cortex of the brain. The cortex of the brain has a consistency somewhat like gelatin. The electrode array of FIG. 1 is pressed into the cortex with tips 34 being inserted first until base 30 comes into contact with the cortical tissue. If the electrodes 32 are slowly pushed into the cortical tissue, the tissue tends to deform and dimple under the array. However, if the array is rapidly inserted by a sharp impulse force, the electrodes 32 penetrate the cortical tissue without substantial deformation of the tissue.

The impact inserter of FIG. 21 includes a delivery tube 160, a piston 162, an insertion mass 164, and an end spring 166. Delivery tube 160 is a cylindrical tube, which may be formed, for example, of aluminum. Piston 162 is a cylindrical mass sized to slidingly fit within tube 160. In a working model of the inserter of FIG. 21, tube 160 has an inside diameter of 0.477 cm and a length of 17.4 cm. Piston 162 has an outside diameter of 0.468 cm. and a mass of 1.76 grams. In the illustrated embodiment, piston 162 is formed of stainless steel. The electrode array is placed on face 168 of insertion mass 164 with electrodes 32 pointing away from face 168.

A pressure tube 170 connects to tube 160 at cap 172. Before the array is inserted into the cortex, piston 162 is held in the position shown in FIG. 21 by means of a vacuum being presented in tube 170 behind piston 162. When it is desired to insert the array into the cortex, an air pressure pulse is supplied to tube 170 to force piston 162 to slide toward insertion mass 164. The small cylindrical extension 174 on piston 162 enters a cylindrical channel 176, formed in tube 160 and strikes the rear face 178 of insertion mass 164. Insertion mass 164 has a mass of 0.9 grams. Insertion mass 164 accepts momentum transfer from piston 162 to achieve a high velocity impact insertion of the array into the cortex. After the array has been inserted into the cortex, spring 166 returns insertion mass 164 to its original position. Spring 166 also controls the distance of travel of insertion mass 164 after it has been struck by piston 162. Useful values for the pressure applied at tube 170 for insertion is a value of 12 pounds per square inch of pneumatic pressure applied for a period of 0.13 seconds.

Figure 22:
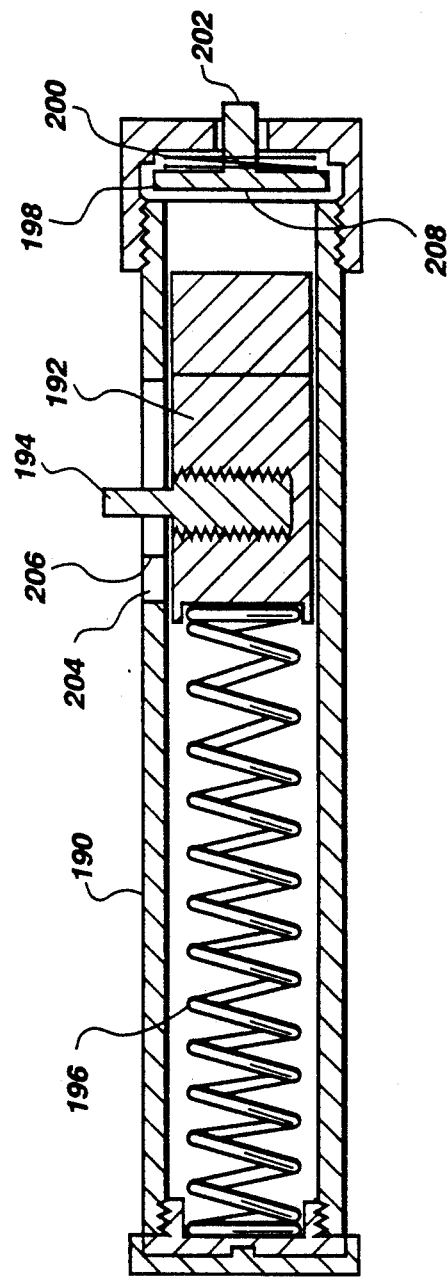
FIG. 22 is a side view of a mechanical implant inserter of the invention.

FIG. 22 illustrates an alternative impact inserter for electrode arrays of the invention. The impact inserter of FIG. 22 uses a mechanical spring rather than pneumatic pressure to achieve insertion. The impact inserter includes a cylinder 190, a sliding plunger 192, a trigger 194, a spring 196, an insertion mass 198, and a spring 200. The array is placed on face 202 of the mass 198 with the electrodes pointing away from face 202. The user grasps cylinder 190 and pulls back trigger 194, which is connected to plunger 192, to thereby withdraw plunger 192 to a position where trigger 194 may be rotated to move into a notch 204. In notch 204, trigger 194 is held in place against face 206 by spring 196. To insert the array, the user rotates trigger 194 out of notch 204. Spring 196 then urges plunger 192 rapidly toward insertion mass 198 to strike mass 198 on face 208, to deliver momentum to mass 198 and to thereby quickly insert the array into the cortex.

While both the inserters of FIGS. 21 and 22 are useful, it is currently believed that the pneumatic inserter of FIG. 21 is preferable, as providing greater control over the parameters of insertion and providing for more consistent insertion results.

Reference herein to details of the illustrated embodiment is not intended to limit the scope of the appended claims, which themselves recite those features regarded important to the invention.

What is claimed:

1. A three-dimensional electrode device for placing electrodes in close proximity to cells lying at least about 1000 microns below a tissue surface, comprising:
   a base of rigid material;
   a plurality of elongated tapered electrodes of a first material mounted to said base to extend away from said base, said electrodes being electrically isolated from each other at said base by means of a second material positioned between said electrodes, each of said electrodes being at least about 1000 microns in length and having a distal end; and
   signal connection means linked with said electrodes for providing electrical connection to each of said electrodes individually.

2. A three-dimensional electrode device according to claim 1 wherein said signal connection means includes an electrical gate associated with each of said electrodes.

3. A three-dimensional electrode device according to claim 2 wherein said electrical gates are multiplexed to be electrically addressable individually.

4. A three-dimensional electrode device according to claim 3, wherein said electrical gates are located on the side of said base opposite the side from which said electrodes extend.

5. A three-dimensional electrode device according to claim 1 wherein said distal ends include a charge transfer material.

6. A three-dimensional electrode device according to claim 1 wherein said first material is a semiconductor material.

7. A three-dimensional electrode device according to claim 6 wherein said second material is a semiconductor doped with an impurity to provide a pn junction at interfaces between said first conducting material and said second material.

8. A three-dimensional electrode device according to claim 6 wherein said second material is glass.

9. A neuron interface device for placing the tips of electrodes in close proximity to cells lying at least about 1000 microns below a tissue surface, comprising:
   a rigid base;
   a plurality of semiconductor electrodes mounted to said base to extend away from said base, said electrodes having parallel longitudinal axes and being electrically isolated from each other at said base, wherein said electrodes are at least about 1000 microns in length, said electrodes having distal ends located distal to said base and being tapered toward said distal ends to present a plurality of electrode tips; and
   electric connection means connected to said electrodes to present electrical signals to said electrodes individually.

* * * * *